(12) United States Patent
Ishii et al.

(10) Patent No.: US 7,534,566 B2
(45) Date of Patent: May 19, 2009

(54) NUCLEIC ACID LABELING METHOD AND LIQUID COMPOSITION

(75) Inventors: Mie Ishii, Machida (JP); Tomohiro Suzuki, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 75 days.

(21) Appl. No.: 11/016,872

(22) Filed: Dec. 21, 2004

(65) Prior Publication Data

US 2005/0186595 A1 Aug. 25, 2005

(30) Foreign Application Priority Data

Dec. 25, 2003 (JP) .............................. 2003-430805

(51) Int. Cl.
*C12Q 1/68* (2006.01)
*C12P 19/34* (2006.01)
*C07H 21/02* (2006.01)

(52) U.S. Cl. .......................... 435/6; 435/91.2; 536/23.1

(58) Field of Classification Search .................. None
See application file for complete search history.

(56) References Cited

U.S. PATENT DOCUMENTS

| | | | |
|---|---|---|---|
| 6,410,229 B1 | 6/2002 | Lockhart et al. | 435/6 |
| 6,569,671 B1 | 5/2003 | Okamoto et al. | 435/285.1 |
| 6,589,737 B1 | 7/2003 | Gruber et al. | 435/6 |
| 6,664,051 B1 | 12/2003 | Shinoki et al. | 435/6 |
| 6,686,439 B2 | 2/2004 | Kenmoku et al. | 528/272 |
| 6,737,238 B2 | 5/2004 | Suzuki et al. | 435/6 |
| 6,803,444 B2 | 10/2004 | Suzuki et al. | 528/361 |
| 6,861,496 B2 | 3/2005 | Kenmoku et al. | 528/272 |
| 2001/0055114 A1 | 12/2001 | Suzuki et al. | 356/317 |
| 2002/0068282 A1 | 6/2002 | Okamoto et al. | 435/6 |
| 2003/0198952 A9 | 10/2003 | Okamoto et al. | 435/6 |
| 2003/0228613 A1* | 12/2003 | Bornarth et al. | 435/6 |
| 2004/0018552 A1 | 1/2004 | Okamoto et al. | 435/6 |
| 2004/0241643 A1 | 12/2004 | Yamamoto et al. | 435/5 |
| 2005/0059069 A1 | 3/2005 | Suzuki et al. | 435/6 |

FOREIGN PATENT DOCUMENTS

| | | |
|---|---|---|
| JP | 3-210197 | 9/1991 |
| JP | 3001919 | 11/1999 |
| JP | 2001-128683 | 5/2001 |
| WO | WO 98/23776 | 6/1998 |
| WO | WO 00/37680 | 6/2000 |

OTHER PUBLICATIONS

Bickmore et al. Visualizing the spatial relationships between defined DNA sequences and the axial region of extracted metaphase chromosomes. Cell. Jan. 12, 1996;84(1):95-104.*
Yu et al. Cyanine dye dUTP analogs for enzymatic labeling of DNA probes. Nucleic Acids Res. Aug. 11, 1994;22(15):3226-32.*
Genome Biol. 2001; 2(11): research0047.1-research0047.7. Published online Oct. 18, 2001.*
M. Schena, et al., "Quantitative Monitoring of Gene Expression Patterns with a Complimentary DNA Microarray", Science, vol. 270, Oct. 20, 1995, pp. 467-470.
T. Lion et al., "Nonradioactive Labeling of Probe with Digoxigenin by Polymerase Chain Reaction", Analytical Biochemistry, vol. 188, 1990, pp. 335-337.
"Fluorescent DNA Labeling by PCR", Application Note # 62, Amersham Biosciences, 1999, pp. 1-8.
Erlich, et al., "Recent Advances in the Polymerase Chain Reaction", Science, vol. 252, Jun. 21, 1991, pp. 1643-1651.

* cited by examiner

*Primary Examiner*—Young J Kim
*Assistant Examiner*—Samuel Woolwine
(74) *Attorney, Agent, or Firm*—Fitzpatrick, Cella, Harper & Scinto.

(57) ABSTRACT

It is provided a nucleic acid labeling method that can reduce to a minimum the amount of a labeling substance used and can effectively incorporate the labeling substance into a product, a target nucleic acid to be detected. In the labeling of a target nucleic acid sequence in a product while it is amplified by PCR, at least one type from among four types of substrates A, T, C and G is chosen as a substrate to be labeled, the concentration of the chosen substrates is adjusted to be lower than that of the non-chosen substrates, and at least the labeled substrates are contained in the chosen substrates.

6 Claims, 1 Drawing Sheet

FIGURE
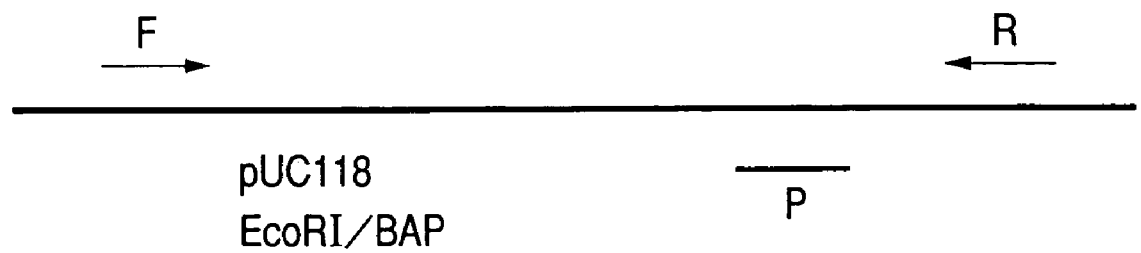

NUCLEIC ACID LABELING METHOD AND LIQUID COMPOSITION

BACKGROUND OF THE INVENTION

1. Field of the Invention

The present invention relates to a labeled PCR product used for a DNA chip, and also to a method for labeling sample nucleic acid and a liquid composition used for nucleic acid labeling. The present invention further relates to a highly sensitive detection method for specimen.

2. Related Background Art

As typified by the human genome project, genes of various types of organisms have been clarified. Association of genes with mechanisms of vital activities, diseases, constitutions, and other factors have successively been examined. As a result, it has been found out that by determining the presence or absence of a specific gene or its expression level (abundance), diseases can be characterized or classified in more detail and effective therapeutic methods therefor can be chosen.

Many methods for determining the presence or absence of a specific gene or its abundance contained in a sample have been proposed over a long period of time. Among them, a method that chooses a specific partial sequence of a target gene or nucleic acid and examines the presence or absence of the partial sequence or the amount in a sample is widely used to know the presence or abundance of such a gene because of its wide applicability. More specifically, this method comprises preparing a nucleic acid (probe) corresponding to a complementary strand of the chosen partial sequence and detecting hybridization between the sample and the probe by any means, so as to determine the presence or absence of the nucleic acid sequence in the sample.

Detection of a specific nucleic acid using hybridization can be carried out either in a solid phase or in a liquid phase. When hybridization is carried out on a solid substrate, a typical method is to immobilize or adsorb a probe on the solid substrate, and then add thereto a sample labeled with a certain labeling substance enabling detection, so that detection is carried out by measuring the signal of the labeling substance on the solid substrate. In particular, a representative form used in solid-phase hybridization is a chip in which one or more probes are immobilized or adsorbed on a planar substrate such as a glass or metal, or a bead carrying a probe immobilized on the surface of a fine particle. The reason why solid-phase hybridization is preferable is that B/F separation is easy, the detection region can physically be made very small whereby high sensitivity is expected, plural types of probes can be separated physically thereby enabling simultaneous detection of multi-items, and handling and application area easy because of the solid phase.

As disclosed in U.S. Pat. No. 6,410,229, for example, a labeled sample nucleic acid is reacted with oligo DNA synthesized on a planar substrate, and the hybridization is measured by fluorescence detection, so as to detect the presence or absence of a specific nucleic acid in a sample or the amount thereof. Japanese Patent Application Laid-Open No. 2001-128683 discloses preparation of a DNA array using a substrate provided with amino groups to detect a 22-mer single-stranded labeled DNA.

In the aforementioned methods for a detecting specific nucleic acid using hybridization, the sample nucleic acid should be labeled. One method for incorporating a labeling substance into a sample is to add a labeled deoxynucleotide (e.g. Cy3-dUTP) in polymerase chain reaction (PCR).

In that case, four types of deoxynucleotides (dATP, dCTP, dGTP, and dTTP; generically called dNTP) and a labeled deoxynucleotide (e.g. Cy3-dUTP) are prepared for the substrates in PCR where the final concentrations of all the dNTPs may be made the same. In Japanese Patent No. 3,001,919, for example, one of the four types of substrate nucleotides is partly replaced by a fluorescence-labeled nucleotide to label the product.

As described above, a detection method utilizing solid-phase hybridization is advantageous in that it is more sensitive than other detection methods. However, the need for detection of a trace amount of nucleic acid is exceeding it, and thus, further improvements of such detection method are required for realizing much higher specific detection with higher sensitivity. Various attempts have been made to improve detection performance. One method is to design a probe to increase the Tm value of the probe-target hybrid, so as to enhance the ability of the probe to bind the target. Another method is labeling of the target with a substance emitting a strong signal, or intensify the labeling substance itself using several labeling substances (sensitizers).

However, the method of enhancing the binding ability of a probe to the target may cause non-specific adsorption or binding, and may significantly decrease specificity in some cases. Thus, the advantage of such a method is limited. On the other hand, the method of amplifying the signal of a labeling substance may significantly decrease the S/N ratio or quantitativeness in some cases. Thus, the advantage of such a method is also limited.

Accordingly, it has been strongly desired to develop a method of efficient incorporation of a labeling substance into a sample which enables more efficient nucleic acid detection. Conventional methods of incorporating a labeling substance into a sample described in the above, in which a labeled deoxynucleotide is added during PCR, has a problem that not so much labeling substance is incorporated into the amplified product since a large amount of non-labeled deoxynucleotide is present as a substrate in PCR, and the detection amount by hybridization may not correspond to the amount of the synthesized amplified product.

In the case of a labeling method using dNTPs in the same final concentrations, if the proportion of the labeled deoxynucleotide is increased to a certain extent, the labeling substance is efficiently incorporated. However, labeled deoxynucleotides are extremely expensive, and thus, the application range thereof may be limited.

SUMMARY OF THE INVENTION

It is an object of the present invention to provide a nucleic acid labeling method that can effectively incorporate the labeling substance into a product (a target nucleic acid to be detected), reducing the amount of a labeling substance used as much as possible, so as to solve the aforementioned problems.

As a result of an intensive study to achieve the aforementioned object, the present inventors have found out that when a labeled deoxynucleotide is added to one of four substrate deoxynucleotides, if the concentration of the chosen, but not-labeled deoxynucleotide is adjusted lower than that of other nucleotides to increase the ratio of the labeled deoxynucleotide, the labeling substance (labeled deoxynucleotide) can be efficiently incorporated into the product. Thus the present invention was completed.

An aspect of the present invention is a nucleic acid labeling method for amplifying a target nucleic acid by a polymerase chain reaction (PCR) while incorporating a labeling substrate into a product, characterized in that a reaction solution for PCR contains four deoxynucleotide substrates of base species A, T, C and G, and one to three substrates are chosen for labeling, and a concentration of each chosen substrate is adjusted to be lower than that of any non-chosen substrate, where each chosen substrate comprises a non-labeled deoxynucleotide and a labeled deoxynucleotide.

Another aspect of the present invention is a method for detecting a target nucleic acid by reacting a sample containing a target nucleic acid with a probe immobilized on a solid substrate, and detecting the target nucleic acid hybridized with the probe immobilized on the solid substrate utilizing a labeling substance incorporated in the target nucleic acid, characterized in that the target nucleic acid is a labeled PCR product prepared by a nucleic acid labeling method according to the above method.

Still another aspect of the present invention is a liquid composition which comprises four types of deoxynucleotides of base species A, T, C and G for use in an amplification of a target nucleic acid by PCR while incorporating a labeled substrate into a product, wherein one to three substrates are chosen for labeling, and a concentration of each chosen substrate is adjusted to be lower than that of any non-chosen substrate, where each chosen substrate comprises a non-labeled deoxynucleotide and a labeled deoxynucleotide.

An aspect of the present invention is a kit for detecting a target nucleic acid, which comprises the following (A) to (C): (A) PCR primers for the amplification of a target nucleic acid; (B) a liquid composition comprising four types of deoxynucleotides of base species A, T, C and G for use in an amplification of a target nucleic acid by PCR while incorporating a labeled substrate into a product, wherein one to three substrates are chosen for labeling, and a concentration of each chosen substrate is adjusted to be lower than that of any non-chosen substrate, where each chosen substrate comprises a non-labeled deoxynucleotide and a labeled deoxynucleotide; and (C) a solid phase probe having a probe disposed on a solid substrate for reacting with the target nucleic acid.

The solid phase probe is preferably a DNA microarray.

When a target nucleic acid is amplified by PCR while a labeling substance is incorporated into a product according to the nucleic acid labeling method of the present invention, where the chosen substrate including a labeled deoxynucleotide and non-labeled deoxynucleotide is set such that the concentration of the non-labeled deoxynucleotide substrate is lower than that of other not-chosen substrate nucleotides, so that the labeling substance can be efficiently incorporated into the product. Furthermore, the method of the present invention for detecting a target nucleic acid enables improvement of detection sensitivity for the target nucleic acid by solid-phase hybridization.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawing, which is incorporated in and constitutes a part of the specification, and serves to explain the invention together with the description.

FIGURE illustrates two primers and one probe for pUC118 EcoRI/BAP. The arrows indicate the 5'-3' direction of each primer.

DESCRIPTION OF THE PREFERRED EMBODIMENTS

Preferred embodiments of the present invention will now be described in detail with the accompanying drawing.

The nucleic acid labeling method of the present invention comprises amplifying a target nucleic acid by PCR (polymerase chain reaction) while incorporating a labeling substrate into the amplification product (a product), which is characterized in that, among four deoxynucleotide substrates of dATP (deoxyadenosine triphosphate), dTTP (deoxythymidine triphosphate), dCTP (deoxycytidine triphosphate) and dGTP (deoxyguanosine triphosphate), one to three substrates are chosen to be labeled, and each concentration of the chosen substrates is adjusted to be lower than that of any non-chosen substrate, and each chosen substrate includes a labeled deoxynucleotide and a non-labeled deoxynucleotide. Specifically, the total concentration of the chosen substrate including the non-labeled deoxynucleotide and the labeled deoxynucleotide is adjusted to be lower than that of any non-chosen substrate. A product is prepared by PCR amplification using such labeling conditions, so that a target nucleic acid can efficiently incorporate a labeling substance in the amplification process.

Moreover, as the concentration of the labeled deoxynucleotide increases, it is advantageous for the incorporation of the labeling substance. When the concentration of the labeled deoxynucleotide contained in the chosen substrate is adjusted to be 20 μM or higher in a PCR reaction solution, the present invention is more effective. It is preferable to prepare a product in such conditions that the concentration of each non-chosen substrate is adjusted to between 150 μM and 300 μM in a PCR reaction solution, and the concentration of the chosen substrate is adjusted to be between 5% and 80% by mole of that of the non-chosen substrate, and in the chosen substrate the molar ratio of the labeled deoxynucleotide to the non-labeled deoxynucleotide is adjusted to 0.25 or greater. More preferably, the chosen substrate is adjusted to be between 10 mol. % and 40 mol. % of the respective non-chosen substrates. Further more preferably, in the chosen substrate the ratio (in terms of the number of moles) of the labeled substrate to the non-labeled substrate is adjusted to 1 or more. When a product is prepared under such conditions, even using a smaller quantity of the labeled substrate, a labeling substance can be efficiently incorporated into a target nucleic acid.

The type of a labeling substance is not particularly limited, and any labeling substances can be used in the present invention. In general, fluorescent substances capable of performing highly sensitive detection or the like are used. Of these, a CyDye (trade name, manufactured by Amersham Bioscience) such as Cy3 and Cy5 is commonly used as a fluorescent substance for labeling nucleic acid. These fluorescent substances are particularly effective in the present invention. In addition, nucleic acid labeling substances such as biotin and an aminoallyl compound are also effective for the product preparation method of the present invention.

A target nucleic acid prepared by the labeling method of the invention can be for detection by hybridization on a solid substrate. Although the amount of the target nucleic acid prepared by the method of the invention may decrease, it is especially effective when used with a detection device for detecting a product of a small amount with high sensitivity, in particular, with a DNA microarray. It is preferable that the area of a single spot of a DNA microarray be $10^{-6}$ m$^2$ less. The lower limit of the spot area can be set depending on the sensitivity of a measurement apparatus such as a scanner used for an analytic purpose of interest. For example, the spot area can be reduced to approximately $10^{-12}$ m$^2$.

The present invention also provides a liquid composition to be used in the above preparation method.

The nucleic acid labeling method of the present invention will be described more in detail.

In the nucleic acid labeling method of the present invention, when a nucleic acid as a target is amplified by PCR, among four deoxynucleotides of dATP, dTTP, dCTP and dGTP used as substrates for PCR, one to three types of substrates are chosen for labeling. The concentration of the chosen substrate is adjusted to be lower than that of the non-chosen substrates, and the chosen substrate contains at least a labeled deoxynucleotide. For a substrate chosen to be labeled, both labeled deoxynucleotide and non-labeled deoxynucleotides are used in combination. The concentration of the non-labeled deoxynucleotide is adjusted to be lower than that of the substrates that are not chosen as those to be labeled, and thus, the proportion of the labeled deoxynucleotide is increased, so that the labeled substrate can be efficiently incorporated.

Moreover, by adjusting the total concentration of the chosen substrate lower than that of any non-chosen substrates, the effect is increased. For instance, when dTTP is chosen as a substrate for labeling, and the total concentration of dTTP and labeled dUTP is adjusted to be lower than that of not chosen substrates dATP, dCTP, and dGTP (the concentration of dTTP+labeled dUTP<the concentration of dATP, dCTP or dGTP).

The relationship between the chosen substrate and the non-chosen substrate is independently applied to each substrate. For instance, when two types of substrates are chosen, each of the two types of chosen substrates satisfies such a relationship in concentration with each of the two non-chosen substrates.

The term "substrate" is used herein to mean substrates for PCR, that is, one of dATP, dTTP, dCTP and dGTP.

The optimum concentration of deoxynucleotides for DNA polymerase (Ex Taq manufactured by TaKaRa, etc.) in PCR is considered to be approximately 200 µM. In general, because of the substrate specificity of the enzyme, incorporation of a chemically labeled deoxynucleotide is less than the ordinary deoxynuceleotides. Thus, it is preferable that the total concentration of the labeled and non-labeled deoxynucleotides is adjusted to 100 µM, and the concentration of the labeled deoxynucleotide is adjusted to 50 µM, for example. As a result, a larger amount of labeling compound is incorporated into the PCR product. By reducing the amount of the chosen non-labeled deoxynucleotide, the reaction is attenuated, and the bulky labeled deoxynucleotide, inherently difficult to incorporate, can be incorporated into the PCR product. Further, the product preparation method of the present invention is tolerant to fluctuation of the quantities of deoxynucleotides by approximately 30%.

Hence, it is preferable that the concentration of substrate chosen for labeling (the total concentration of the labeled and non-labeled deoxynucleotides) is adjusted to from 5% to 80% by mole, more preferably from 10% to 40% by mole of the concentration of the substrates not chosen for labeling. Moreover, the concentration of the substrate(s) not chosen for labeling is preferably from 150 µM to 300 µM. Furthermore, the concentration of the substrate(s) chosen for labeling (the total concentration of the labeled and non-labeled deoxynucleotides) is preferably 20 µM or higher. Still further, the mole rato of the labeled deoxynucleotide to the non-labeled deoxynucleotide in the substrate chosen for labeling is adjusted to 0.25 or greater, and preferably be 1 or greater, but preferably not larger than about 50.

The nucleotide length of the PCR-amplified product having the nucleotide sequence of a target nucleic acid is not particularly limited. However, it is particularly effective when the nucleotide length is between 100 bp and 2,000 bp.

As a labeling substance, a fluorescent substance or the like can be used. In particular, CyDye (manufactured by Amersham Bioscience), including Cy3 and Cy5 as typical examples, is commonly used as a fluorescent substance for labeling nucleic acid. These fluorescent substances are particularly effective in the present invention. In addition, biotin, aminoallyl and the like are also effective for the nucleic acid labeling method of the present invention. Since biotin is smaller than Cy3 in molecular size, its steric hindrance in PCR is rather small. However, incorporation of biotin into the PCR product can be enhanced by the method of the present invention. As a deoxynucleotide to be labeled, thyminidine is commonly used and many labeling reagents corresponding to thymidine are commercially available. The present invention can also be applied to them.

A target nucleic acid labeled by the labeling method of the present invention hybridizes with a probe immobilized on the surface of a solid substrate and becomes a double stranded. The signal of a labeling substance in the target nucleic acid bound to the probe is measured, thereby performing highly sensitive detection. Highly sensitive detection devices of various materials and forms utilizing solid-phase hybridization are known, and the present invention can be applied to them without any limitation. A representative example of such devices is a DNA microarray formed by immobilizing nucleic acid on a glass substrate. Such a DNA microarray can be particularly preferably used to detect a target nucleic acid prepared by the method of the present invention. Materials usable for the solid substrate may include a resin, a metal, a thin metal film, and a fiber. Examples of the shapes of a solid substrate may include a fine particle, a fiber-optic edge, a porous material, and a fiber.

There are various methods of binding a probe to a solid substrate, such as adsorption or chemical bond. Any binding method can be applied in the present invention. In the case of ionic bond, for example, native nucleic acid can be bound to the surface of a glass or resin substrate coated with an amino group by merely adding the nucleic acid thereto. Alternatively, modified oligonucleotides having a functional group such as an amino group or thiol group on the 5' or 3' end. When an amino group is used, for example, succinimide group efficiently reactive with the amino group is immobilized beforehand on the surface of the solid substrate, and an amino-modified oligonucleotide is added to the surface of the solid substrate to form a covalent bond. The bonded oligonucleotide can be preferably used as a probe for detecting the target nucleic acid of the present invention. When the oligonucleotide is modified to have a thiol group, for example, a maleimide group is introduced to the solid substrate form a covalent bond with oligonucleotide as easy as in the case of using an amino group. The bonded oligonucleotide can be preferably used as a probe for detecting the target nucleic acid of the present invention. A DNA solution can be supplied onto the solid substrate by ink-jet printing. A DNA microarray produced by the ink-jet printing is characterized by the very small probe spots. The S/N ratio is an important factor for detection. A target nucleic acid amplified by the labeling method of the present invention contains more labeling compound per target molecule. Accordingly, it also has an effect of improving the S/N ratio, and thus, it is particularly effective.

Moreover, the labeling method of the present invention is not only effective for single PCR in which only one type of target is amplified, but also effective for multiple PCR, or asymmetric PCR in which the concentrations of primers are differently set to actively amplify either one of the strands.

Furthermore, a liquid composition containing deoxynucleotides used for the nucleic acid-labeling method of the present invention can also be provided in the form of a diagnostic kit or PCR premix. Such a liquid composition comprise an aqueous medium mainly made of water suitable for PCR, a combination of deoxynucleotides as described above, components necessary for the enzyme function, and various additives for provide the salt concentration necessary for primer annealing, specifically, Tris-Cl, KCl, $(NH_4)_2SO_4$, $MgCl_2$ etc.

Thus, by the labeling method of the present invention, a target sequence to be detected in a sample can be amplified and labeled. Accordingly, the labeling method of the present invention can be preferably used as a method of preparing a labeled product to be used with an analysis method in which a labeled nucleic acid product is hybridized with a probe, such as solid-phase hybridization.

Furthermore, the present invention provides a kit for detecting a target nucleic acid, comprising the following components (A) to (C):
(A) PCR primers used to amplify a target nucleic acid;
(B) a liquid composition comprising four types of deoxynucleotides A, T, C and G, wherein from one to three types of deoxynucleotides are chosen from the four types of deoxynucleotides, the concentration of each chosen deoxynucleotide is adjusted to be lower than that of any non-chosen deoxynucleotide, and each chosen deoxynucleotide contains a labeled deoxynucleotide; and
(C) a probe for reacting with the above target nucleic acid disposed on a solid substrate. The solid phase probe is preferably a DNA microarray.

According to the above constitution, the detection kit enables highly sensitive detection of a target nucleic acid.

EXAMPLES

The present invention will be more specifically described in the following examples. However, the following examples involve only several examples of the best mode for carrying out the present invention, and are not intended to limit the scope of the present invention.

Example 1

I. PCR of pUC118 EcoRI/BAP (1) Design of Primers

The following two primers were designed based on the sequence of a commercially available vector pUC118 EcoRI/BAP (3,162 bp) (TaKaRa). The information regarding the entire nucleotide sequence of pUC118 EcoRI/BAP was available from TaKaRa or open database and the like. Primers were designed taking into full consideration sequences, GC %, and ds melting temperature (Tm value), such that a desired partial nucleotide sequence in pUC118 EcoRI/BAP could ba specifically and efficiently amplified by PCR amplification using the primers.

The thus designed two primers are a forward primer (F) and a reverse primer (R). Using pUC118 EcoRI/BAP as a template, PCR amplification was carried out using F and R in combination, so as to amplify a 1,324-bp PCR product. The nucleotide sequence and Tm value of the designed primers are shown in Table 1.

TABLE 1

| Name | Nucleotide sequence | Tm (° C.) |
|---|---|---|
| F | 5' TGATTTGGGTGATGGTTCACGTAG 3' | 60.9 |
| R | 5' ATCAGCAATAAACCAGCCAGCC 3' | 61.5 |

The positions of the two types of primers (F and R) and a probe (P) in the full length pUC118 EcoRI/BAP are shown in FIGURE. In the FIGURE, the arrow indicates the 5' to 3' direction of each primer.

(2) Synthesis of Primers

The two primers designed in Example 1 (1) were synthesized. Each primer was prepared synthesizing a DNA chain of the predetermined sequence by using a conventional method and a DNA synthesizer. The products were subjected to cartridge purification, so as to obtain two types of primers. The obtained primers were diluted with a TE buffer to 10 μM.

(3) PCR Amplification

A PCR amplification was carried out using the two primers synthesized in above (2), the vector pUC118 EcoRI/BAP manufactured by TaKaRa as a template, and a commercial PCR kit (TaKaRa Ex Taq, Takara Bio Inc.) This PCR kit includes a dNTP mixture consisting of four deoxynucleotides dATP, dCTP, dTTP, and dGTP (2.5 mM each). In order to adjust respective concentrations, Sequencing Grade Solution dNTPs manufactured by Amersham Bioscience were used. In addition, in order to label the PCR product with fluorescence, Cy3-dUTP manufactured by Amersham Bioscience was used, so that the product was labeled with Cy3. dNTP mixtures were prepared with solutions of non-labeled deoxynucleotides, of which concentrations in the mixtures are shown in Table 2. For comparison, a dNTP mixture (STd.) was prepared by the conventional method.

TABLE 2

| | Compositions of dNTP mixtures | | | | | | |
|---|---|---|---|---|---|---|---|
| | Std. | Mix1 | Mix2 | Mix3 | Mix4 | MiX5 | Mix6 |
| dATP | 5.0 mM | 5.0 mM | 5.0 mM | 5.0 mM | 5.0 mM | 5.0 mM | 5.0 mM |
| dCTP | 5.0 mM | 5.0 mM | 5.0 mM | 5.0 mM | 5.0 mM | 5.0 mM | 5.0 mM |
| dGTP | 5.0 mM | 5.0 mM | 5.0 mM | 5.0 mM | 5.0 mM | 5.0 mM | 5.0 mM |
| dTTP | 5.0 mM | 4.0 mM | 2.0 mM | 1.0 mM | 0.5 mM | 0.25 mM | 0 mM |

PCR amplification was carried out using a forward primer and a reverse primer described in (1) above. Reaction solutions shown in Table 3 were prepared using dNTP mixtures (Std., Mix1-Mix6) shown in Table 2 in accordance with the protocols described below.

TABLE 3

| Composition of reaction solution | |
|---|---|
| Component | Composition |
| Takara Ex Taq | 0.5 μl (2.5 U) |
| 10× Ex Taq Buffer (20 mM Mg$^{2+}$) | 5.0 μl |
| Template DNA (Takara pUC118 dilution) | 1.0 μl (10 ng) |
| Forward Primer (F) | 2.5 μl (25 pmol/tube) |
| Reverse Primer (R) | 2.5 μl (25 pmol/tube) |
| dNTP Mixture (Std., Mix1-Mix6) | 2.0 μl (*) |

TABLE 3-continued

Composition of reaction solution

| Component | Composition |
|---|---|
| Cy3 dUTP(1.0 mM, manufactured by Amersham Bioscience) | 2.0 µl (40 µM) |
| H₂O | 34.5 µl |
| Total | 50 µl |

(*) Since Mix1 to Mix6 and Std. are different in dTTP concentration, final concentrations of labeled and non-labeled dNTPs are shown Table 4, separately.

The dNTP concentrations in the reaction solutions prepared as shown in Table 3 are shown in the following Table 4. dATP, dCTP, and dGTP were contained at a concentration of 200 µM in Table 4, which was the same with the later Examples.

TABLE 4

Concentrations of deoxynucleotides in reaction solutions

| | Std. | A (Mix1) | B (Mix2) | C (Mix3) | D (Mix4) | E (MIx5) | F (Mix6) |
|---|---|---|---|---|---|---|---|
| dATP, dCTP, dGTP | 200 µM | 200 µM | 200 µM | 200 µM | 200 µM | 200 µM | 200 µM |
| dTTP | 200 µM | 160 µM | 80 µM | 40 µM | 20 µM | 10 µM | 0 µM |
| Cy3-dUTP | 40 µM | 40 µM | 40 µM | 40 µM | 40 µM | 40 µM | 40 µM |
| dTTP + Cy3-dUTP | 240 µM | 200 µM | 120 µM | 80 µM | 60 µM | 50 µM | 40 µM |

Each of the thus prepared reaction solutions was subjected to a PCR amplification using a commercially available thermal cycler in accordance with the temperature cycle protocols shown in the following Table 5.

TABLE 5

Temperature conditions in PCR amplification

| Step | Temperature | Retention time | Number of repetition |
|---|---|---|---|
| 1 | 94° C. (denaturation) | 30 sec. | 25 cycles |
| 2 | 55° C. (annealing) | 45 sec. | |
| 3 | 72° C. (extension) | 1 min. | |
| 4 | 72° C. | 10 min. | |

After completion of the amplification reaction, the PCR-amplified product was purified using a purification column (QIAGEN QIAquick PCR Purification Kit). After completion of the purification, the PCR-amplified product solution was adjusted to 50 µl. A portion of the purified PCR-amplified product solution was then electrophoresed by conventional methods, so as to confirm that a band of a desired nucleotide length appeared for each of the 7 types of PCR products. The concentrations of the PCR-amplified products are shown in Table 6.

TABLE 6

Concentrations of PCR-amplified products

| | Std. | A(Mix1) | B (Mix2) | C (Mix3) | D(Mix4) | E(Mix5) | F(Mix6) |
|---|---|---|---|---|---|---|---|
| Concentration of product | 51.0 nM | 47.9 nM | 30.1 nM | 14.2 nM | 9.6 nM | 3.0 nM | 0 nM |

As shown in Table 6, the larger the amount of dTTP in the reaction solution was, the larger the amount of the obtained PCR-amplified product became.

II. Production of DNA Microarray (1) Design and Synthesis of Probe

A probe was designed for the aforementioned PCR product A taking into full consideration sequences, GC %, and melting temperature (Tm value) so as to enable specific recognition of a designed partial nucleotide sequence.

The nucleotide sequence and Tm value of the designed probe are shown in Table 7.

TABLE 7

| Name | Nucleotide sequence | Tm (° C.) |
|---|---|---|
| P | 5' GATAAAGTTGCAGGACCACTTCTGC 3' | 75.7 |

In this probe design, a DNA strand extending from the R primer hybridized with a probe, so as to form a hybrid with the probe.

(2) Cleaning of Glass Substrate

A substrate made from synthetic quartz glass (size (W×L×T): 25 mm×75 mm×1 mm; manufactured by Iiyama Precision Glass Co., Ltd.) was placed in a heat-resistant alkali-resistant rack. The rack was then immersed in a cleaning solution used for ultrasonic cleaning, which had been adjusted to have a predetermined concentration. After the rack was immersed in the cleaning solution overnight, it was subjected to ultrasonic cleaning for 20 minutes. Subsequently, the glass substrate was taken out of the solution, and it was gently rinsed with pure water. Thereafter, it was subjected to ultrasonic cleaning in extra pure water for 20 minutes. Thereafter, the glass substrate was immersed in a 1 N sodium hydroxide aqueous solution heated to 80° C., for 10 minutes. After rinsing with pure water and then with extra pure water, a cleaned quartz glass substrate for DNA chip was prepared.

(3) Surface Treatment

A silane coupling agent KBM-603 (manufactured by Shin-Etsu Chemical Co., Ltd.) was dissolved in pure water to a concentration of 1%. The obtained solution was stirred at room temperature for 2 hours. Subsequently, the cleaned quarts glass substrate was immersed in the silane coupling agent aqueous solution, and it was left at room temperature for 20 minutes. Thereafter, the glass substrate was pulled out of the solution, and the surface of the substrate was then gently cleaned with pure water. Thereafter, nitrogen gas was blown onto both sides of the glass substrate for drying. Subsequently, the glass substrate dried by nitrogen gas blowing was baked in an oven at 120° C. for 1 hour, so as to complete the treatment with the silane coupling agent. As a result of the treatment with the silane coupling agent, an amino group derived from the silane coupling agent was introduced into the surface of the glass substrate.

Meanwhile, N-maleimidocaproyloxysuccinimide manufactured by Dojindo Laboratories ((N-(6-maleimidocaproyloxy)succinimide); hereinafter abbreviated as EMCS) was dissolved in a 1:1 mixed solvent consisting of dimethyl sulfoxide and ethanol, to a final concentration of 0.3 mg/ml, so as to prepare an EMCS solution. After completion of the baking, the glass substrate treated with the coupling agent was left to cool, and it was then immersed in the prepared EMCS solution at room temperature for 2 hours. During this immersion treatment, the amino group that had been introduced into the surface of the glass substrate by coupling agent treatment was reacted with a succinimide group of EMCS, so that a maleimide group derived from EMCS was introduced into the surface of the glass substrate. The glass substrate was pulled out of the EMCS solution, and washed with the aforementioned mixed solvent consisting of dimethyl sulfoxide and ethanol. Thereafter, the substrate was washed with ethanol, and then dried in a nitrogen gas atmosphere.

(4) Synthesis of Probe DNA

The probe designed in II(1) above was synthesized.

After that, in order to allow the probe DNA to covalently bind to the above glass substrate into the surface of which a maleimide group had been introduced, the 5'-terminus thereof was modified with thiol according to conventional methods. Thereafter, protecting groups, which had been introduced for preventing side reactions during DNA synthesis, were removed from the probe DNA, and HPLC purification and desalination treatment were then conducted.

The obtained probe DNA was dissolved in pure water, and the obtained solution was divided, such that each probe DNA had a final concentration of 10 μM (when it was dissolved in an ink). The probe DNA was then freeze-dried to remove water.

(5) Discharge of Probe DNA with BJ Printer and Binding of Probe DNA to Substrate Surface An aqueous solution containing 7.5%-by-mass glycerin, 7.5%-by-mass thiodiglycol, 7.5%-by-mass urea, and 1.0%-by-mass acetylenol EH (manufactured by Kawaken Fine Chemicals Co., Ltd.) was prepared. Subsequently, the divided probe DNA was dissolved in the aforementioned mixed solvent, such that it had a predetermined concentration (10 μM). The obtained probe DNA solution was filled in an ink tank used for a bubble-jet printer (product name: BJF-850; manufactured by Canon Inc.), and it was then installed in a print head.

It is to be noted that the aforementioned bubble-jet printer was modified such that it enabled ink-jet printing onto a planar plate. Moreover, by inputting a printing pattern according to a certain file preparation method, the modified bubble-jet printer can spot an approx. 5-pl droplet of the DNA solution at a pitch of approximately 120 μm.

Subsequently, using the modified bubble-jet printer, the probe DNA solution was spotted on the surface of the glass substrate. A printing pattern had previously been prepared such that 16 spots of a probe were discharged on a single DNA microarray, and ink-jet printing was then conducted. It was confirmed with a magnifying glass or the like that the DNA solution was certainly spotted to obtain a pattern of interest. Thereafter, the glass substrate was left at rest in a humidifying chamber at ordinary temperature for 30 minutes, so that a maleimide group existing on the surface of the glass substrate was allowed to react with a sulfanyl group (—SH) existing at the 5'-terminus of the probe DNA.

(6) Washing

After completion of the reaction that was carried out for 30 minutes in the humidifying chamber, an unreacted probe DNA portion remaining on the surface of the glass substrate was washed out with a 10 mM phosphate buffer (pH 7.0) containing 100 mM NaCl. Thus, a DNA microarray-type DNA chip was obtained, wherein certain single-stranded probe DNA was immobilized on each of 16 spots per DNA chip on the surface of the glass substrate.

(III) Hybridization Reaction

Using the DNA microarray produced in (II) above and seven PCR-products produced as product nucleic acid in (I) above, hybridization was carried out on a microarray.

(1) Blocking of DNA Microarray

BSA (bovine serum albumin fraction V; manufactured by Sigma) was dissolved in 100 mM NaCl/10 mM phosphate buffer, so that it became 1% by mass. The DNA microarray produced in (II) above was immersed in the obtained solution at room temperature for 2 hours, so that the surface of the glass substrate was blocked. After completion of the blocking, the glass substrate was washed with a 0.1×SSC solution (15 mM NaCl, 1.5 mM sodium citrate (trisodium citrate dihydrate, $C_6H_5Na_3.2H_2O$), pH 7.0) containing 0.1%-by-mass SDS (sodium dodecyl sulfate), and then rinsed with pure water. Thereafter, water was removed from the DNA microarray using a spin dry device.

(2) Preparation of Hybridization Solution

A hybridization solution for each PCR product of the following constitution was prepared. Each PCR-amplified product solution was used at an amount of 2.0 μl and made to a final volume of 120 μl.

<Hybridization Solution>
6×SSPE/10% formamide/PCR product solution (6×SSPE: 900 mM NaCl, 60 mM $NaH_2PO_4.H_2O$, 6 mM EDTA, pH 7.4)

(3) Hybridization

After water was removed, the DNA chip was installed in a hybridization device (Genomic Solutions Inc. Hybridization Station). Using the hybridization solution of the aforementioned composition, a hybridization reaction was carried out with procedures and conditions described in the following Table 8.

TABLE 8

| Conditions and procedures for hybridization | |
|---|---|
| Operation | Operational procedures and conditions |
| Reaction | 65° C. 3 min → 92° C. 2 min → 55° C. 4 h |
| Washing | 2 × SSC/0.1% SDS at 25° C. |
|  | 2 × SSC at 20° C. |
| (Rinsing) | $H_2O$ (manual rinsing) |
| Drying | Spin dry |

(4) Fluorescence Measurement

After completion of the hybridization reaction, the DNA chip was spin-dried, and the fluorescence of the hybrid on the DNA chip was measured by using a fluorescence detection apparatus for DNA microarrays (manufactured by Axon, Genepix 4000B). The results of the fluorescence intensity determined for each of the PCR-amplified products Std. and A to F are shown in Table 9 below. To calculate the intensity, the fluorescence intensity measured at a portion where no probe DNA spots existed on the DNA chip was used as a background value, and the background value was subtracted from the apparent fluorescence intensity of each spot. The obtained value was defined as the actual fluorescence intensity. Measurement was carried out twice, and the average is shown in the following table 9.

Subsequently, a hybridization reaction was carried out under the hybridization conditions and procedures shown in Table 8. In addition, the fluorescence measurement described in Example 1 III(4) was carried out for each DNA chip. The mean values are shown in Table 10.

TABLE 9

Concentration after PCR-amplification and fluorescence intensity after hybridization

| | Std. | A (Mix1) | B (Mix2) | C (Mix3) | D (Mix4) | E (Mix5) | F (Mix6) |
|---|---|---|---|---|---|---|---|
| Concentration of product | 51.0 nM | 47.9 nM | 30.1 µM | 14.2 nM | 9.6 nM | 3.0 nM | 0 nM(*) |
| Fluorescence intensity | 3243 | 5052 | 10565 | 29659 | 29948 | 16956 | 176 |

(*)The concentration of the product was below the detection limit.

From the results shown in Table 9, it was found out that although the synthesized amount of each of the PCR-amplified products A to E was smaller than that of Std. produced by the conventional method, the fluorescence intensity thereof after hybridization was higher than that of Std., that is, the samples A to E was very efficiently labeled with the labeling substance. In other words, even when the amount of a labeling substance added to the PCR reaction solution was small, if the total concentration of the labeled and not-labeled deoxynucleotides of the chosen base species was adjusted to be lower than that of other not-chosen nucleotides, the labeling substance was efficiently incorporated in the PCR product. However, if the concentration of the not-labeled deoxynucleotide was zero, almost no PCR amplification occurred, and the product was not detected by hybridization (sample F). From these results, it was shown that the concentration of not-labeled deoxynucleotide of the base species chosen for labeling (herein dTTP) is adjusted to between 5 mol % and 80 mol % of the concentration of the deoxynucleotide of the base species not chosen for labeling (herein dATP, dCTP, and dGTP), nucleic acid is efficiently labeled by PCR amplification.

Moreover, as shown in Table 9, the hybrids of samples C and D showed fluorescent intensity approximately 10 times greater than that of Std. produced by the conventional method. That is, in the nucleic acid labeling method of the present invention, the concentration of non-labeled deoxynucleotides (herein dTTP) in nucleotides to which labeled deoxynucleotides are added is adjusted to be between 10 mol % and 40 mol % of the concentration of deoxynucleotides (herein dATP, dCTP, and dGTP) in nucleotides to which labeled deoxynucleotides are not added, thereby most efficiently carrying out nucleic acid labeling. It should be noted that a labeling substance is incorporated for only one type of the base species in this Example, but the same effect is obtained when a plurality of labeling substances are incorporated for a plurality of the base species.

Example 2

The PCR products A-D shown in Table 6 in Example 1 were adjusted to an equimolar concentration. Then, a hybridization solution (final 120 µl) was prepared using 2 µl each of the PCR-amplified product solutions, thereby resulting in a final concentration indicated below.

<Hybridization Solution>
6×SSPE/10% formamide/PCR-amplified product solution (6×SSPE: 900 mM NaCl, 60 mM $NaH_2PO_4·H_2O$, 6 mM EDTA, pH 7.4)

TABLE 10

Fluorescence intensity of hybridized PCR-products

| | A (Mix1) | B (Mix2) | C (Mix3) | D (Mix4) |
|---|---|---|---|---|
| Fluorescence intensity | 5052 | 14351 | 60530 | 63600 |

From these results, it was confirmed that a much larger amount of the labeling substance was incorporated in a single-stranded samples C and D in comparison with sample A. In addition, it was also found out that when the ratio of the labeled deoxynucleotides to the non-labeled deoxynucleotides is 1 or greater, it is more effective.

Example 3

Three PCR reaction solutions were prepared in accordance with Table 3 such that the concentrations of deoxynucleotides became as shown in Table 11. Thereafter, a PCR amplification reaction was carried out under the temperature conditions shown in Table 5.

TABLE 11

Concentrations of deoxynucleotides in PCR reaction solution

| | G (Mix7) | H (Mix8) | C (Mix3) |
|---|---|---|---|
| dATP, dCTP, dGTP | 200 µM | 200 µM | 200 µM |
| dTTP | 100 µM | 60 µM | 40 µM |
| Cy3-dUTP | 100 µM | 60 µM | 40 µM |
| dTTP + Cy3-dUTP | 200 µM | 120 µM | 80 µM |

The concentrations of the PCR-amplified products are shown in Table 12.

TABLE 12

Concentrations of PCR-amplified products

| | G (Mix7) | H (Mix8) | C (Mix3) |
|---|---|---|---|
| Concentration of product | 35.0 nM | 26.4 nM | 14.2 nM |

The larger the amount of dTTP in the reaction solution was, the larger the amount of the PCR-amplified product became.

A hybridization solution was prepared using each of the PCR-amplified products shown in Table 12 under the same conditions as in Example 1, thereby resulting in a final concentration indicated below. Each PCR-amplified product solution was used at an amount of 2.0 µl to a final volume of 120 µl.

<Hybridization Solution>
6×SSPE/10% formamide/PCR-amplified product solution (6×SSPE: 900 mM NaCl, 60 mM $NaH_2PO_4.H_2O$, 6 mM EDTA, pH 7.4)

Subsequently, a hybridization reaction was carried out under the hybridization conditions and procedures described in Table 8. In addition, the fluorescence measurement as in Example 1 III(4) was carried out, and fluorescence of each DNA chip was determined. The mean values are shown in Table 13.

TABLE 13

Fluorescence intensity of PCR-amplified products

|  | G (Mix7) | H (Mix8) | C (Mix3) |
|---|---|---|---|
| Fluorescence intensity | 24447 | 35457 | 29659 |

These results show that H showed the highest fluorescence intensity in hybridization. Thus, even when the ratio of the labeled deoxynucleotide to the non-labeled deoxynucleotide was made 1 in PCR, higher incorporation efficiency is obtained with a smaller amount of labeling substance when the concentration of the non-labeled deoxynucleotide was made lower than those of other nucleotides as with samples H and C.

Example 4

Five reaction solutions were prepared in accordance with Table 3, such that the concentrations of deoxynucleotides were as shown in Table 14. Thereafter, a PCR amplification reaction was carried out under the temperature conditions shown in Table 5. That is, labeling of nucleic acid was carried out using these reaction solutions where the concentration of the non-labeled nucleotides A, C or G was varied.

TABLE 14

Concentrations of deoxynucleotides in reaction solutions

|  | I (Mix 9) | J (Mix10) | C (Mix3) | K (Mix11) | L (Mix12) |
|---|---|---|---|---|---|
| dATP, dCTP, dGTP | 100 µM | 150 µM | 200 µM | 250 µM | 300 µM |
| dTTP | 40 µM | 40 µM | 40 µM | 40 µM | 40 µM |
| Cy3-dUTP | 40 µM | 40 µM | 40 µM | 40 µM | 40 µM |
| dTTP + Cy3-dUTP | 80 µM | 80 µM | 80 µM | 80 µM | 80 µM |

The concentrations of PCR-amplified products are shown in Table 15.

TABLE 15

Concentrations of PCR-amplified products

|  | I (Mix9) | J (Mix10) | C (Mix3) | K (Mix11) | L (Mix12) |
|---|---|---|---|---|---|
| Concentration of product | 10.7 nM | 13.5 nM | 14.2 nM | 14.8 nM | 14.3 nM |

The concentration of the PCR-amplified product is relatively low in sample I (Mix9), but in other samples, the concentrations of the PCR-amplified products are almost the same.

Hybridization solutions were prepared using the PCR-amplified products shown in Table 14 under the same conditions as in Example 1. Each PCR-amplified product solution was used at an amount of 2.0 µl to a final volume of 120 µl.

<Hybridization Solution>
6×SSPE/10% formamide/PCR-amplified product solution (6×SSPE: 900 mM NaCl, 60 mM $NaH_2PO_4.H_2O$, 6 mM EDTA, pH 7.4)

Subsequently, a hybridization reaction was carried out with the hybridization conditions and procedures described in Table 8. After that, the fluorescence measurement as in Example 1 III(4) was carried out, and fluorescence of each DNA chip was determined. The mean values are shown in Table 16.

TABLE 16

Fluorescence intensity of PCR-amplified products

|  | I (Mix9) | J (Mix10) | C (Mix3) | K (Mix11) | L (Mix12) |
|---|---|---|---|---|---|
| Amount of product | 8073 | 22369 | 29659 | 26758 | 26239 |

These results show that almost the same fluorescent intensity was obtained with Samples J, C, K and L except for Sample I. That is, labeling efficiency does not depend on the concentrations of nucleotides not selected for labeling, and that it is adequate to adjust the concentration thereof to be between 150 µM and 300 µM.

The present invention is not limited to the above embodiments and various changes and modifications can be made within the spirit and scope of the present invention. Therefore to apprise the public of the scope of the present invention, the following claims are made.

This application claims priority from Japanese Patent Application No. 2003-430805 filed on Dec. 25, 2003, which is hereby incorporated by reference herein.

What is claimed is:

1. A method of detecting a presence of a target nucleic acid in a sample comprising the steps of:
   (i) conducting a polymerase chain reaction in a solution so as to amplify said target nucleic acid;
   (ii) hybridizing an amplified product resulting from said step (i) with a probe which specifically hybridizes with an amplicon of said target nucleic acid; and
   (iii) detecting a signal from said probe resulting from said step (ii), said signal originating from a label incorporated in said target nucleic acid,
   wherein said solution comprises a deoxynucleotide mixture consisting of:
   (a) dATP, dCTP, dGTP and dTTP; or
   (b) dATP, dCTP, dGTP, dTTP and dUTP,
   wherein, in the mixture described in (a), one type of deoxynucleotide chosen from the mixture comprises a labeled deoxynucleotide and a non-labeled deoxynucleotide,
   wherein, in the mixture described in (b), dUTP comprises a labeled deoxynucleotide and dTTP comprises a non-labeled deoxynucleotide,
   wherein the molar ratio of the labeled deoxynucleotide to the non-labeled deoxynucleotide is 1 or greater, and
   wherein the total concentration of the labeled deoxynucleotide and the non-labeled deoxynucleotide in the solution is lower than that of any other deoxynucleotide in the solution.

2. A method for detecting a presence of a target nucleic acid in a sample comprising the steps of:
   (i) conducting a polymerase chain reaction so as to amplify said target nucleic acid in a solution comprising a deoxynucleotide mixture consisting of:
   (a) non-labeled and labeled dATP and non-labeled dNTPs, where N is C, G and T, a total concentration of said non-labeled and labeled dATP in said solution being lower than those of said non-labeled dNTPs, and a molar ratio of said labeled dATP to said non-labeled dATP being 1 or greater;
   (b) non-labeled and labeled dCTP and non-labeled dNTPs, where N is A, G and T, a total concentration of said non-labeled and labeled dCTP in said solution being lower than those of said non-labeled dNTPs, and a molar ratio of said labeled dCTP to said non-labeled dCTP being 1 or greater;
   (c) non-labeled and labeled dGTP and non-labeled dNTPs, where N is A, C and T, a total concentration of said non-labeled and labeled dGTP in said solution being lower than those of said non-labeled dNTPs, and a molar ratio of said labeled dGTP to said non-labeled dGTP being 1 or greater;
   (d) non-labeled and labeled dTTP and non-labeled dNTPs, where N is A, C and G, a total concentration of said non-labeled and labeled dTTP in said solution being lower than those of said dNTPs, and a molar ratio of said labeled dTTP to said non-labeled dTTP being 1 or greater; or
   (e) non-labeled dTTP and labeled dUTP, and non-labeled dNTPs, where N is A, C and G, a total concentration of said non-labeled dTTP and labeled dUTP in said solution being lower than those of said dNTPs, and a molar ratio of said labeled dUTP to said non-labeled dTTP being 1 or greater;
   (ii) hybridizing an amplified product resulting from said step (i) with a probe which specifically hybridizes with an amplicon of said target nucleic acid; and
   (iii) detecting a signal from said probe resulting from said step (ii), said signal originating from a label incorporated in said target nucleic acid.

3. A process for detecting a presence of a target nucleic acid in a sample comprising the steps of:
   (i) conducting a polymerase chain reaction in a solution comprising dATP, dGTP, dCTP, dTTP and labeled dUTP, so as to amplify said target nucleic acid, a total concentration of dTTP and labeled dUTP in said solution being lower than those of dATP, dGTP and dCTP, and a molar ratio of labeled dUTP to dTTP in said solution being 1 or greater;
   (ii) hybridizing an amplified product resulting from said step (i) with a probe which specifically hybridizes with an amplicon of said target nucleic acid, said probe being immobilized on a solid substrate; and (iii) detecting a signal from said probe resulting from said step (ii), said signal originating from a label incorporated in said target nucleic acid.

4. The detection method according to claim 1, wherein said probe is disposed on a solid substrate as a DNA microarray.

5. The detection method according to claim 1, wherein said probe is an oligonucleotide.

6. The detection method according to claim 1, wherein said target nucleic acid has a base length of between 100 bp and 2000 bp.

* * * * *

SEQUENCE LISTING

<160> NUMBER OF SEQ ID NOS: 3

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1

-continued

```
tgatttgggt gatggttcac gtag                                    24

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
atcagcaata aaccagccag cc                                      22

<210> SEQ ID NO 3
<211> LENGTH: 25
<212> TYPE: DNA
<213> ORGANISM: Artificial Sequence
<220> FEATURE:
<223> OTHER INFORMATION: Probe

<400> SEQUENCE: 3
gataaagttg caggaccact tctgc                                   25
```